United States Patent [19]

Brown

[11] 4,064,965
[45] Dec. 27, 1977

[54] STETHOSCOPE

[76] Inventor: Alberta Mae Brown, 1241 W. 53rd St., Los Angeles, Calif. 90037

[21] Appl. No.: 666,178

[22] Filed: Mar. 11, 1976

[51] Int. Cl.² .............................................. A61B 7/02
[52] U.S. Cl. .................................... 181/131; 181/135
[58] Field of Search ............... 181/126, 129, 131, 132, 181/135, 137

[56] References Cited

U.S. PATENT DOCUMENTS

| 977,503 | 12/1910 | Baylis | 181/131 |
|---|---|---|---|
| 1,657,078 | 1/1928 | Frederick et al. | 181/131 |
| 2,142,407 | 1/1939 | Norton et al. | 181/135 |
| 2,807,328 | 9/1957 | Gould | 181/131 |
| 3,867,925 | 2/1975 | Ersek | 181/131 |
| 3,934,674 | 1/1976 | Shore et al. | 181/131 |

FOREIGN PATENT DOCUMENTS

| 278,513 | 10/1927 | United Kingdom | 181/131 |

Primary Examiner—Stephen J. Tomsky
Attorney, Agent, or Firm—Francis X. LoJacono, Sr.

[57] ABSTRACT

A stethoscope having a plurality of connector plugs positioned between the head set unit and the sound pick-up diaphragm unit wherein the connector plugs are removably attached to each other by a tubular yoke which provides communication between the head set and the sound pick-up diaphragm, whereby the sound emitted by the diaphragm is transmitted through the connector plugs into the head set in a normal manner.

3 Claims, 3 Drawing Figures

STETHOSCOPE

BACKGROUND OF THE INVENTION

1. Field of the Invention

This invention relates generally to a stethoscope and, more particularly, to a stethoscope having removable connector plugs, whereby the head set and the sound pick-up diaphragm can be readily interchanged or removed from each other.

2. Description of the Prior Art

As is well known in the art, various problems and difficulties are encountered in the use of the presently designed stethoscopes. That is, there is no provision to allow for simple connecting and disconnecting of the head-set unit with the lower sound-transmitting unit.

Generally, the head-set unit of the known type comprises a pair of elongated, curvilinear, rigid tubular members which are movably joined by a flexible clamp to allow the tubular members to be spread apart at the time of use, whereby the head set is positioned to engage the ears of the individual. Each tubular member is provided at one end with a plug; and the opposite ends thereof are directly coupled to various types of flexible hoses, which are generally formed from a soft plastic or rubber. The opposite terminating end of the hose is connected to a sound pick-up diaphragm.

Due to the continuous use of such an instrument, the hose members thereof lose their flexibility and become inoperative.

To the applicant's knowledge, there is no device of this character that is provided with simple removable connectors that allow for changing of the parts of a stethoscope. However, the following description of the applicant's invention will show how the above problems have been overcome.

SUMMARY OF THE INVENTION

The present invention comprises a stethoscope of the type well known in the medical field, having a hand set which includes two oppositely-disposed, rigid tubular members with ear plugs secured at one end of each member, the opposite ends thereof being connected to removable connector plug. A flexible spring-like coupling strut interconnects each rigid tubular member holding them in juxtaposition to each other, whereby the tubular members must be forced apart to be used.

Thus, each lower end of the tubular members have female connector plugs secured thereto in which a male connector member is removably received therein. The male member is formed as a "Y-shaped" tubular yoke having three connecting ends. Hence, two ends are coupled to the female plugs secured to the head set, while the third male end of the yoke is coupled to an additional female connector plug which is part of the elongated flexible tube that leads to and is adapted to receive any well known sound pick-up diaphragm.

OBJECTS AND ADVANTAGES OF THE INVENTION

The present invention has for an important object a provision wherein a stethoscope is provided with connector plugs disposed between the head set and the sound pick-up diaphragm, whereby each unit can be interchanged or very easily separated for cleaning, sterilizing or replacing of worn sections thereof.

It is another object of the invention to provide a stethoscope of this character that is easy to service and maintain.

It is still another object of the invention to provide a stethoscope of this character wherein the sound pick-up diaphragm unit can be separated and left in a particular patient's room when the patient is under a quarantine condition.

It is a further object of the invention to provide a stethoscope of this character that is relatively inexpensive to manufacture.

It is still a further object of the present invention to provide a device of this character that is simple and rugged in construction.

The characteristics and advantages of the invention are further sufficiently referred to in connection with the accompanying drawings, which represent one embodiment. After considering this example, skilled persons will understand that variations may be made without departing from the principles disclosed and I contemplate the employment of any structures, arrangements or modes of operation that are properly within the scope of the appended claims.

DESCRIPTION OF THE DRAWINGS

Referring more particularly to the accompanying drawings, which are for illustrative purposes only.

DESCRIPTION OF THE PREFERRED EMBODIMENT

Figure 1:
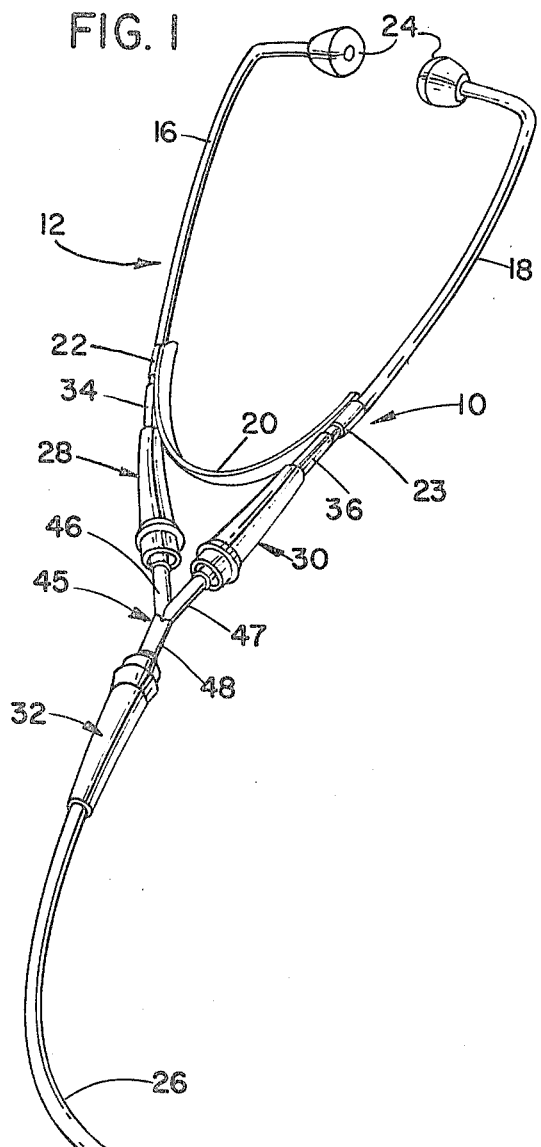
FIG. 1 is a perspective view of the present invention.

Referring more particularly to the drawings, there is shown in FIG. 1 a stethoscope, generally indicated at 10. As is well known in the medical field, the stethoscope is an instrument used for the detection and study of sounds within the body (such as the chest and abdomen) that are conveyed to the ears of the observer through tubing connected to a head set unit, designated at 12, at one end thereof and a sound pick-up diaphragm unit, designated at 14, connected to the opposite end thereof, said sound pick-up diaphragm being placed upon the area to be examined.

There are various types of head sets 12 and the unit herein shown comprises a pair of elongated, curvilinear, rigid tubular members 16 and 18, respectively. The tubular members 16 and 18 are held in an inwardly-biased, juxtaposed relationship, as seen in FIG. 1. Thus, in this particular illustration the biasing means is provided by a spring-like coupling strut 20 secured at each end 22 and 23 to respective tubular members 16 and 18.

As is generally the case, there is also provided a pair of ear plugs 24 adapted to be secured to the ends of the tubular members 16 and 18.

Accordingly, the sound pick-up diaphragm is operably connected to the head set through flexible tube 26 formed of a plastic material, wherein a plurality of removable connecting means are interdisposed between the head set 12 and the diaphragm 14. The connector means comprises three female connector plugs 28, 30 and 32, each plug being identical in its construction with the exception that connector plugs 28 and 30 are provided with short extending flexible tubes 34 and 36, respectively. These tubes 34 and 36 can be either bonded to the plugs or molded as one piece.

Likewise, connector plug 32 can be molded to the elongated tube 26 or bonded to one end thereof. However, each female connector is formed having a somewhat truncated body 40, the smaller end thereof being secured to its respective tube wherein the tube is received in a central bore 42, the opposite end of the body terminating with an enlarged head portion 44, said bore 42 also being enlarged within the head 44.

Figure 2:
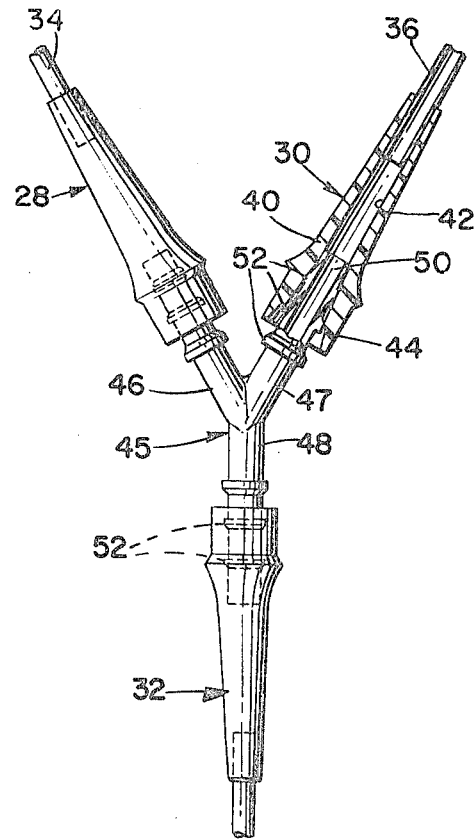
FIG. 2 is an enlarged plan view of the connector plugs, wherein one of the plugs is shown in cross-section.
Figure 3:
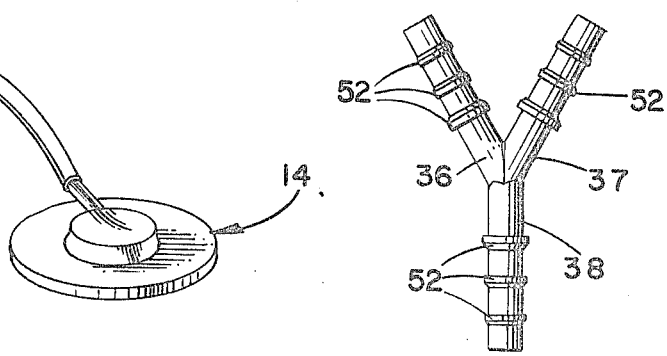
FIG. 3 is an elevational view of the male yoke member of the connector plug.

Thus, in order to interconnect connector plugs 28 and 30 to plug 32, there is included a "Y"-shaped yoke connecting member, indicated generally at 45. The yoke comprises three leg extending male members 46, 47 and 48 which are integrally formed having communicating passages 50, as seen in FIG. 2. Legs 46 and 48 are adapted to be inserted within respective plugs 28 and 30, while leg 48 is received in plug 32. Thus, sound picked up by diaphragm 14 is transmitted through tube 26 into each respective tubular head member 16 and 18 in the well known manner.

Each leg 46, 47 and 48 has a plurality of annular ribs 52 disposed thereon, whereby they provide the necessary frictional grip within the enlarged area of bore 42 of the plugs 28, 30 and 32. It should be also noted that each rib 52 is formed so that the following rib is progressively larger in diameter to provide a positive connection within each respective plug, yet still allows for simple removal therefrom when required. The invention and its attendant advantages will be understood from the foregoing description and it will be apparent that various changes may be made in the form, construction and arrangement of the parts of the invention without departing from the spirit and scope thereof or sacrificing its material advantages, the arrangement herein before described being merely by way of example, and I do not wish to be restricted to the specific form shown or uses mentioned, except as defined in the accompanying claims.

I claim:

1. In combination with a stethoscope of the type including a head set and a sound-pick-up diaphragm used to detect sounds produced in the body, the improvement comprises:

a plurality of removable connector plugs wherein at least two of said plugs are secured to the head set, and wherein at least one of said plugs is attached to sound-pick-up diaphragm, each of said plugs having a central bore disposed therein for communication therethrough, and between said head set and said sound-pick-up diaphragm, each of said connector plugs including an extended, flexible, tubular member affixed to one end thereof for permanent attachment of the respective head set and sound-pick-up diaphragm, and wherein an enlarged, tapered opening is arranged in the opposite ends of said plugs;

an integrally formed, tubular, yoke member having interconnecting passages disposed therein, said yoke being formed to be removably coupled to each of said plugs, whereby sound is transmitted from said diaphragm to said head set when said diaphragm is positioned for contact with the body, said yoke member comprising three extended leg members formed in a substantially "Y"-shaped configuration; and engaging means integrally formed about said leg members for removable engagement within said enlarged end of said bore of said connector plugs, thereby allowing said head set and said sound pick-up to be connected or disconnected when required, and wherein other sound-pick-up diaphragms can be readily interchanged with said head set.

2. The combination as recited in claim 1, wherein said connector plugs also include:

a truncated body wherein the reduced diameter end is integrally formed with said extended flexible tubular member, and wherein the opposite end thereof is provided with an enlarged head whereby said tube can be readily held for connecting or disconnecting said plug with respect to said yoke member.

3. The combination as recited in claim 2, wherein the engaging means disposed on each of said extended leg members comprises a plurality of annular rib members for positive internal engagement with said bore of said connector plug.

* * * * *